United States Patent
Barbero et al.

(10) Patent No.: US 11,327,076 B2
(45) Date of Patent: May 10, 2022

(54) BIOMARKERS OF THERAPEUTIC RESPONSIVENESS

(71) Applicant: Meso Scale Technologies, LLC., Rockville, MD (US)

(72) Inventors: Simone Barbero, Germantown, MD (US); Eli N. Glezer, Del Mar, CA (US); Anu Mathew, North Potomac, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 176 days.

(21) Appl. No.: 16/157,341

(22) Filed: Oct. 11, 2018

(65) Prior Publication Data

US 2019/0265243 A1 Aug. 29, 2019

Related U.S. Application Data

(60) Continuation of application No. 15/488,743, filed on Apr. 17, 2017, now abandoned, which is a division of application No. 14/168,629, filed on Jan. 30, 2014, now abandoned.

(60) Provisional application No. 61/759,431, filed on Feb. 1, 2013.

(51) Int. Cl.
*G01N 33/574* (2006.01)
*A61K 31/5377* (2006.01)
*C12Q 1/42* (2006.01)
*C12Q 1/48* (2006.01)

(52) U.S. Cl.
CPC ... *G01N 33/57415* (2013.01); *A61K 31/5377* (2013.01); *C12Q 1/42* (2013.01); *C12Q 1/485* (2013.01); *G01N 2333/912* (2013.01); *G01N 2333/916* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 5,208,535 A | 5/1993 | Nakayama et al. |
| 5,807,522 A | 9/1998 | Brown et al. |
| 6,110,426 A | 8/2000 | Shalon et al. |
| 7,842,246 B2 | 11/2010 | Wohlstadter et al. |
| 2003/0113713 A1 | 6/2003 | Glezer et al. |
| 2003/0207290 A1 | 11/2003 | Kenten et al. |
| 2004/0022677 A1 | 2/2004 | Wohlstadter et al. |
| 2004/0189311 A1 | 9/2004 | Glezer et al. |
| 2005/0052646 A1 | 3/2005 | Wohlstadter et al. |
| 2005/0142033 A1 | 6/2005 | Glezer et al. |
| 2006/0205012 A1 | 9/2006 | Debad et al. |
| 2011/0071042 A1* | 3/2011 | Kim ................ G01N 33/5011 506/9 |
| 2014/0141985 A1 | 5/2014 | Glezer et al. |
| 2014/0221368 A1 | 8/2014 | Barbero et al. |
| 2017/0242012 A1 | 8/2017 | Barbero et al. |

FOREIGN PATENT DOCUMENTS

| | | |
|---|---|---|
| WO | 99/26067 A1 | 5/1999 |
| WO | 2004/058055 A2 | 7/2004 |
| WO | 2007/040559 A2 | 4/2007 |
| WO | 2010/127057 A2 | 11/2010 |
| WO | WO 2010/127057 | * 11/2010 |

OTHER PUBLICATIONS

Gao et al (Bio-Rad 2007 Bulletin).*
Gao et al (ACR Annual Meeting—Apr. 14-18, 2007; Los Angeles, CA, abstract #2824).*
Han et al (PLoS One, 2011, 6:e18691, internet pp. 1-8).*
Corkery et al. (Annals of Oncology, 2009, 20:862-867).*
MSD® Technology Platform (Jul. 2011).*
MSD® Toxicology Applications (Oct. 2011).*
Meso Scale Discovery® Assays and Kits (Mar. 2011).*
Holmes et al (Journal of Clinical Oncology, 2010, 28, No. 15(Suppl), abstract TPS109).*
LoPiccolo et al (Drug Resistance Updates, 2008, 11:32-50).*
Lin et al (British J of Cancer, 2005, 93:1372-1381).*
Dong et al (Cancer Chemother Pharmacol, 2012, 70:707-716).*
Berns A., "Gene Expression in Diagnosis", Cancer 403:491-492 (2000).
Chen R. et al., "Simultaneous Quantification of Six Human Cytokines in a Single Sample Using Microparticle-Based Flow Cytometric Technology", Clinical Chemistry 45(9):1693-1694 (1999).
Delehanty J.B., "Printing Functional Protein Microarrays Using Piezoelectric Capillaries", Methods in Molecular Biology 264:135-143 (2004).
Lovett R.A., "Toxicogenomics: Toxicologists Brace for Genomics Revolution", Science 289(5479):536-537 (2000).
Lue R.Y.P. et al., "Site-Specific Immobilization of Biotinylated Proteins for Protein Microarray Analysis", Methods in Molecular Biology 264:85-100 (2004).
Oberoi P. et al., "Conjugated Antibody Characterization is Critical for Reducing Variability in Immunogenicity and Biomarker Assays", American Assoc. Pharmaceutical Scientists Annual Meeting 2012, Poster M1072 (1 page).

(Continued)

*Primary Examiner* — Laura B Goddard
(74) *Attorney, Agent, or Firm* — Scully, Scott, Murphy & Presser, P.C.

(57) ABSTRACT

The present invention relates to methods of diagnosing breast cancer in a patient, as well as methods of monitoring the progression of breast cancer and/or methods of monitoring a treatment protocol of a therapeutic agent or a therapeutic regimen. The invention also relates to assay methods used in connection with the diagnostic methods described herein.

11 Claims, 4 Drawing Sheets

(56) References Cited

OTHER PUBLICATIONS

Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (2000).
Skates S.J. et al., "Pooling of Case Specimens to Create Standard Serum Sets for Screening Cancer Biomarkers", Cancer Epidemiol Biomarkers Prev. 16(2):334-341 (2007).
Vignali D.A.A., "Multiplexed Particle-Based Flow Cytometric Assays", Journal of Immunological Methods 243:243-255 (2000).
Walt D.R., "Molecular Biology: Bead-Based Fiber-Optic Arrays", Science 287(5452):451-452 (2000).
Meso Scale Discovery® (MSD) Technology, MSD® Technology Platform (16 pages) (Jul. 2011).
MSD® Multi-Spot Assay System, Akt Signaling Panel Whole Cell Lysate Kit (21 pages) (Jun. 2011).
Meso Scale Discovery® Assays and Kits (4 pages) (Mar. 2011).
Meso Scale Discovery® Toxicology Applications (24 pages) (Oct. 2011).
Final U.S. Office Action dated Dec. 19, 2016 received in U.S. Appl. No. 14/168,629.
U.S. Office Action dated Jun. 28, 2016 received in U.S. Appl. No. 14/168,629.
Final U.S. Office Action dated Nov. 6, 2015 received in U.S. Appl. No. 14/168,629.
U.S. Office Action dated Mar. 17, 2015 received in U.S. Appl. No. 14/168,629.
U.S. Office Action dated May 11, 2018 received in U.S. Appl. No. 15/488,743.

\* cited by examiner

Fig. 1

| | IC50 (µM) | 0.03 | 0.13 | 0.23 | 0.34 | 0.38 | 0.78 | 1.25 | 1.7 | 3.3 | 5.7 | 7 | 10 | 10 | 12 | 12 | 12 | 12 |
|---|---|---|---|---|---|---|---|---|---|---|---|---|---|---|---|---|---|---|
| | time post treatment (h) | MB175 | BT474 | HCC1954 | SKBR3 | SUM190 | MB468 | UACC812 | T47D | CAL51 | MB453 | ZR75-1 | HCC1937 | EFM19 | BT20 | MCF7 | MB231 | CAMA1 |
| Akt | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.99 | 0.82 | 0.89 | 1.44 | 0.99 | 1.10 | 1.25 | 0.88 | 1.07 | 1.00 | 0.88 | 0.87 | 1.21 | 0.94 | 0.90 | 1.04 | 0.93 |
| | 0.5 | 0.84 | 0.80 | 0.84 | 1.14 | 1.00 | 1.13 | 1.47 | 0.85 | 0.95 | 0.90 | 0.89 | 1.13 | 0.96 | 1.28 | 1.01 | 1.26 | 1.20 |
| | 1 | 0.63 | 0.85 | 0.76 | 0.72 | 0.88 | 0.88 | 1.23 | 0.84 | 0.86 | 0.88 | 0.87 | 0.89 | 1.20 | 1.19 | 0.98 | 0.33 | 0.87 |
| | 8 | 0.72 | 0.78 | 0.69 | 0.96 | 0.94 | 1.00 | 0.76 | 0.84 | 1.00 | 0.84 | 0.78 | 0.76 | 1.22 | 1.27 | 0.97 | 0.87 | 0.96 |
| | 24 | 0.99 | 0.75 | 0.75 | 1.15 | 0.92 | 1.46 | 0.79 | 0.95 | 0.96 | 0.92 | 0.98 | 1.35 | 1.26 | 1.36 | 1.05 | 1.12 | 1.09 |
| | 48 | 0.39 | 1.33 | 0.83 | 1.21 | 1.17 | 1.23 | 0.87 | 1.20 | 1.18 | 1.04 | 1.27 | 1.36 | 1.35 | 1.53 | 1.09 | 1.46 | 0.84 |
| pAkt | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.20 | 0.08 | 0.84 | 0.34 | 0.58 | 0.71 | 0.60 | 0.64 | 0.84 | 0.65 | 0.95 | 0.70 | 0.90 | 0.53 | 0.74 | 1.17 | 0.73 |
| | 0.5 | 0.09 | 0.18 | 0.64 | 0.23 | 0.65 | 0.47 | 0.39 | 0.57 | 0.89 | 0.20 | 1.22 | 0.90 | 1.09 | 0.89 | 1.01 | 1.05 | 0.65 |
| | 1 | 0.05 | 0.14 | 0.53 | 0.30 | 0.50 | 0.80 | 0.49 | 0.47 | 0.68 | 0.34 | 1.18 | 0.77 | 1.13 | 0.66 | 1.12 | 0.92 | 0.49 |
| | 8 | 0.10 | 0.15 | 0.74 | 0.60 | 0.64 | 1.22 | 0.48 | 0.80 | 1.04 | 1.19 | 1.82 | 0.66 | 2.12 | 0.69 | 1.64 | 1.31 | 0.99 |
| | 24 | 0.14 | 0.50 | 1.00 | 1.20 | 1.04 | 0.98 | 0.56 | 0.92 | 1.01 | 1.81 | 1.99 | 1.02 | 1.28 | 0.86 | 1.58 | 1.82 | 0.91 |
| | 48 | 0.09 | 0.48 | 1.19 | 1.43 | 1.13 | 1.12 | 0.59 | 0.74 | 1.24 | 2.22 | 2.18 | 0.89 | 1.70 | 0.99 | 1.34 | 1.60 | 0.78 |
| p-EGFR | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.97 | 1.30 | 1.04 | 0.79 | 0.81 | 0.74 | 0.82 | 1.18 | 1.02 | 0.91 | 0.74 | 0.85 | 0.99 | 0.83 | 0.70 | 1.11 | 1.11 |
| | 0.5 | 0.69 | 0.99 | 0.87 | 0.73 | 0.89 | 0.63 | 0.76 | 1.19 | 1.02 | 0.66 | 1.07 | 1.14 | 0.89 | 1.15 | 0.75 | 1.11 | 0.97 |
| | 1 | 0.54 | 0.98 | 0.64 | 0.56 | 0.82 | 0.70 | 0.57 | 1.00 | 1.19 | 0.80 | 0.93 | 1.26 | 1.36 | 0.98 | 0.87 | 0.98 | 0.82 |
| | 8 | 0.66 | 0.95 | 0.63 | 0.62 | 0.76 | 0.89 | 0.86 | 0.94 | 0.97 | 0.88 | 0.88 | 1.08 | 1.20 | 0.79 | 0.75 | 1.03 | 0.88 |
| | 24 | 0.97 | 1.15 | 0.69 | 0.87 | 0.90 | 0.90 | 0.57 | 1.16 | 0.71 | 0.83 | 0.93 | 0.96 | 0.65 | 0.64 | 0.56 | 1.54 | 0.77 |
| | 48 | 0.40 | 0.82 | 0.76 | 0.77 | 0.98 | 0.91 | 0.84 | 1.14 | 0.92 | 0.80 | 1.00 | 0.97 | 0.98 | 0.72 | 0.62 | 2.09 | 0.92 |
| p-GSK3b | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.47 | 0.33 | 0.95 | 0.21 | 0.77 | 0.22 | 0.84 | 1.04 | 0.84 | 0.76 | 0.83 | 0.75 | 0.74 | 0.68 | 0.72 | 1.06 | 0.76 |
| | 0.5 | 0.34 | 0.45 | 0.80 | 0.54 | 0.82 | 0.97 | 0.63 | 0.98 | 0.76 | 0.33 | 0.94 | 1.03 | 0.74 | 0.98 | 0.94 | 3.96 | 0.92 |
| | 1 | 0.24 | 0.40 | 0.85 | 0.18 | 0.74 | 0.75 | 0.67 | 0.88 | 0.75 | 0.53 | 0.85 | 1.36 | 0.82 | 0.90 | 0.91 | 5.32 | 0.73 |
| | 8 | 0.28 | 0.59 | 0.88 | 0.35 | 0.74 | 0.33 | 0.85 | 1.12 | 0.90 | 1.27 | 1.00 | 3.31 | 0.81 | 0.99 | 0.73 | 1.81 | 1.02 |
| | 24 | 0.39 | 0.61 | 0.87 | 0.34 | 0.77 | 0.28 | 0.83 | 1.07 | 0.63 | 1.24 | 0.99 | 3.42 | 0.57 | 0.73 | 0.81 | 2.57 | 0.83 |
| | 48 | 0.27 | 0.74 | 0.93 | 0.39 | 0.82 | 0.89 | 1.06 | 0.70 | 0.84 | 1.54 | 1.07 | 0.80 | 0.68 | 0.95 | 0.82 | 0.93 | 0.78 |

Fig. 1(cont'd)

| | IC50 (uM) | 0.03 | 0.13 | 0.23 | 0.34 | 0.36 | 0.78 | 1.25 | 1.7 | 3.3 | 5.7 | 7 | 10 | 10 | 12 | 12 | 12 | 12 |
|---|---|---|---|---|---|---|---|---|---|---|---|---|---|---|---|---|---|---|
| | time post treatment (h) | MB175 | BT474 | HCC1954 | SKBR3 | SUM190 | MB468 | UACC812 | T47D | CAL51 | MB453 | ZR75-1 | HCC1937 | EFM19 | BT20 | MCF7 | MB231 | CAMA1 |
| p-mTOR | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.95 | 0.50 | 1.01 | 0.79 | 0.65 | 0.65 | 1.16 | 1.03 | 0.91 | 0.87 | 0.92 | 0.92 | 1.09 | 0.93 | 0.74 | 0.94 | 0.77 |
| | 0.5 | 0.56 | 0.59 | 0.93 | 0.82 | 0.82 | 0.84 | 0.89 | 1.03 | 0.83 | 0.50 | 1.01 | 1.11 | 1.09 | 1.24 | 0.77 | 0.86 | 0.80 |
| | 1 | 0.43 | 0.49 | 0.83 | 0.51 | 0.74 | 0.70 | 0.91 | 0.92 | 0.78 | 0.57 | 1.06 | 1.52 | 1.04 | 1.16 | 0.80 | 0.80 | 0.67 |
| | 8 | 0.39 | 0.38 | 0.74 | 0.60 | 0.76 | 0.80 | 0.95 | 0.75 | 0.73 | 0.86 | 0.82 | 1.31 | 0.89 | 1.05 | 0.50 | 0.91 | 0.74 |
| | 24 | 0.73 | 0.65 | 0.77 | 1.02 | 0.98 | 0.80 | 0.96 | 0.98 | 0.68 | 1.11 | 1.00 | 1.32 | 0.99 | 1.13 | 0.72 | 1.42 | 0.86 |
| | 48 | 0.48 | 0.93 | 0.86 | 1.03 | 1.21 | 0.84 | 1.13 | 1.01 | 0.99 | 1.22 | 1.16 | 1.72 | 1.03 | 1.22 | 0.82 | 1.48 | 0.94 |
| Raptor | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 1.10 | 1.03 | 0.86 | 0.89 | 0.90 | 1.23 | 1.13 | 0.86 | 0.83 | 1.16 | 0.81 | 0.90 | 0.96 | 0.91 | 1.41 | 1.14 | 1.03 |
| | 0.5 | 1.24 | 1.21 | 0.81 | 0.86 | 0.91 | 1.32 | 0.95 | 0.83 | 0.85 | 1.32 | 0.79 | 0.96 | 0.91 | 1.13 | 1.13 | 1.19 | 1.07 |
| | 1 | 1.10 | 0.97 | 0.75 | 0.87 | 0.97 | 0.89 | 0.90 | 1.06 | 0.77 | 1.60 | 0.75 | 0.61 | 0.82 | 1.02 | 1.06 | 0.91 | 1.06 |
| | 8 | 1.09 | 0.96 | 0.71 | 1.00 | 0.79 | 1.22 | 1.02 | 0.89 | 0.74 | 0.81 | 0.97 | 0.69 | 1.02 | 1.17 | 1.03 | 0.89 | 0.96 |
| | 24 | 1.36 | 0.85 | 0.82 | 0.95 | 0.81 | 1.10 | 0.92 | 0.80 | 0.63 | 1.34 | 0.89 | 0.89 | 1.34 | 1.33 | 1.12 | 0.80 | 1.05 |
| | 48 | 0.81 | 1.06 | 1.04 | 1.13 | 1.00 | 0.95 | 1.13 | 1.05 | 0.81 | 1.49 | 1.13 | 1.30 | 1.33 | 1.32 | 1.01 | 1.48 | 1.19 |
| p-MEK | 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| | 0.17 | 0.13 | 0.48 | 0.89 | 0.41 | 0.33 | 0.84 | 1.09 | 0.74 | 1.09 | 1.05 | 1.05 | 0.53 | 0.52 | 0.84 | 0.81 | 1.11 | 0.44 |
| | 0.5 | 0.13 | 0.55 | 0.88 | 0.63 | 0.28 | 0.89 | 0.82 | 0.89 | 1.77 | 2.16 | 1.15 | 0.85 | 0.48 | 0.89 | 1.52 | 1.17 | 1.72 |
| | 1 | 0.19 | 0.54 | 0.77 | 0.63 | 0.14 | 0.75 | 0.84 | 0.97 | 1.00 | 2.22 | 1.29 | 0.87 | 0.49 | 0.92 | 0.86 | 0.85 | 0.84 |
| | 8 | 0.05 | 0.18 | 0.81 | 1.35 | 0.11 | 0.80 | 1.00 | 1.89 | 0.80 | 1.22 | 1.29 | 1.05 | 0.31 | 1.23 | 0.49 | 1.10 | 0.59 |
| | 24 | 0.06 | 0.24 | 0.56 | 1.20 | 0.17 | 0.67 | 1.86 | 1.68 | 0.70 | 0.86 | 1.77 | 0.81 | 0.38 | 1.05 | 0.61 | 1.35 | 0.36 |
| | 48 | 0.04 | 0.44 | 0.58 | 0.74 | 0.20 | 0.73 | 1.17 | 0.50 | 0.85 | 1.24 | 1.36 | 0.50 | 0.36 | 0.75 | 0.85 | 0.81 | 0.58 |

Fig. 2(a)-(d)

BIOMARKERS OF THERAPEUTIC RESPONSIVENESS

CROSS REFERENCE TO RELATED APPLICATIONS

The present application is a continuation of co-pending application Ser. No. 15/488,743, filed Apr. 17, 2017, which is a divisional of application Ser. No. 14/168,629, filed Jan. 30, 2014, now abandoned, which claims priority of U.S. Provisional Application No. 61/759,431 filed on Feb. 1, 2013, the entire contents of which are incorporated herein by reference.

STATEMENT REGARDING FEDERALLY-SPONSORED RESEARCH

This invention was made with government support under HHSN261201000075C awarded by the National Institutes of Health. The government has certain rights in the invention.

FIELD OF THE INVENTION

This application relates to assay methods useful in the detection and treatment of breast cancer.

BACKGROUND OF THE INVENTION

Challenges in the field of oncology include the lack of efficient means for early cancer detection and for specific cancer subtyping and for measuring and/or predicting responsiveness to therapy. There is a need for new cancer biomarkers that can provide early and specific diagnosis of cancer and enable targeted therapy and prognosis. The need for new diagnostics has been the impetus behind many initiatives targeting the discovery and development of new biomarkers for cancer. The hope is that the identification of suitable biomarkers will allow for the development of early cancer detection screening tests and will lead to improved cancer therapy and a reduction in the mortality associated with many cancers.

SUMMARY OF THE INVENTION

The invention provides a method for evaluating the efficacy of a treatment regimen in a patient diagnosed with breast cancer, said method comprising (a) obtaining a test sample from a patient undergoing said treatment regimen for breast cancer;

(b) measuring a level of a biomarker in said test sample, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof;

(c) comparing said level to a normal control level of said biomarker and (d) evaluating from said comparing step (c) whether said patient is responsive to said treatment regimen.

The invention further provides a method for evaluating the efficacy of a treatment regimen in a patient diagnosed with breast cancer, said method comprising (a) ordering a test comprising a measurement of a level of a biomarker in a test sample obtained from a patient undergoing said treatment regimen for breast cancer, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof;

(b) comparing said level to a normal control level of said biomarker, and (c) evaluating from said comparing step (b) whether said patient is responsive to said treatment regimen.

Another embodiment of the invention is a method of administering a treatment regimen to a patient in need thereof for treating breast cancer, comprising:

(a) obtaining a test sample from a patient undergoing said treatment regimen for breast cancer;

(b) measuring a level of a biomarker in said test sample, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof;

(c) comparing said level to a normal control level of said biomarker;

(d) evaluating from said comparing step (c) whether said patient is responsive to said treatment regimen; and (e) adjusting said treatment regimen based on said evaluating step (d).

Still further, the invention contemplates a method of administering a treatment regimen to a patient in need thereof for treating breast cancer, comprising:

(a) obtaining a test sample from a patient prior to the commencement of said treatment regimen for breast cancer;

(b) measuring a level of a biomarker in said test sample, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof;

(c) comparing said level to a normal control level of said biomarker;

(d) evaluating from said comparing step (c) whether said patient will be responsive to said treatment regimen; and (e) administering said treatment regimen based on said evaluating step (d).

An alternative or additional embodiment of the invention is a method of administering a treatment regimen to a patient in need thereof for treating breast cancer, comprising:

(a) evaluating a level of a biomarker in a test sample obtained from a patient undergoing said treatment regimen for breast cancer relative to a normal control level of said biomarker, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof; and (b) adjusting said treatment regimen based on said evaluating step (a).

Moreover, the invention includes a method of administering a treatment regimen to a patient in need thereof for treating breast cancer, comprising:

(a) evaluating a level of a biomarker in a test sample obtained from a patient prior to the commencement of said treatment regimen for breast cancer relative to a normal control level of said biomarker, wherein said biomarker comprises (i) total and phosphorylated isoforms of Akt, MEK, mTOR, GSK3beta, and combinations thereof, (ii) p70S6K, eIF4EBP1, PTEN, and (iii) combinations thereof; and (b) administering said treatment regimen based on said evaluating step (a).

The invention also provides a kit for the analysis of a breast cancer panel comprising (a) a multi-well assay plate comprising a plurality of wells, each well comprising at least four discrete binding domains to which capture antibodies to the following human analytes are bound: (i) total and phosphorylated isoforms of Akt, MEK, mTOR, GSK3beta, and combinations thereof, (ii) p70S6K, eIF4EBP1, PTEN, and (iii) combinations thereof;

(b) in one or more vials, containers, or compartments, a set of labeled detection antibodies specific for said human analytes; and (c) in one or more vials, containers, or compartments, a set of calibrator proteins.

BRIEF DESCRIPTION OF THE FIGURES

FIG. 1 shows the fractional marker levels (to 0 h time point) for a representative set of biomarkers.

DETAILED DESCRIPTION OF THE INVENTION

Figure 2:
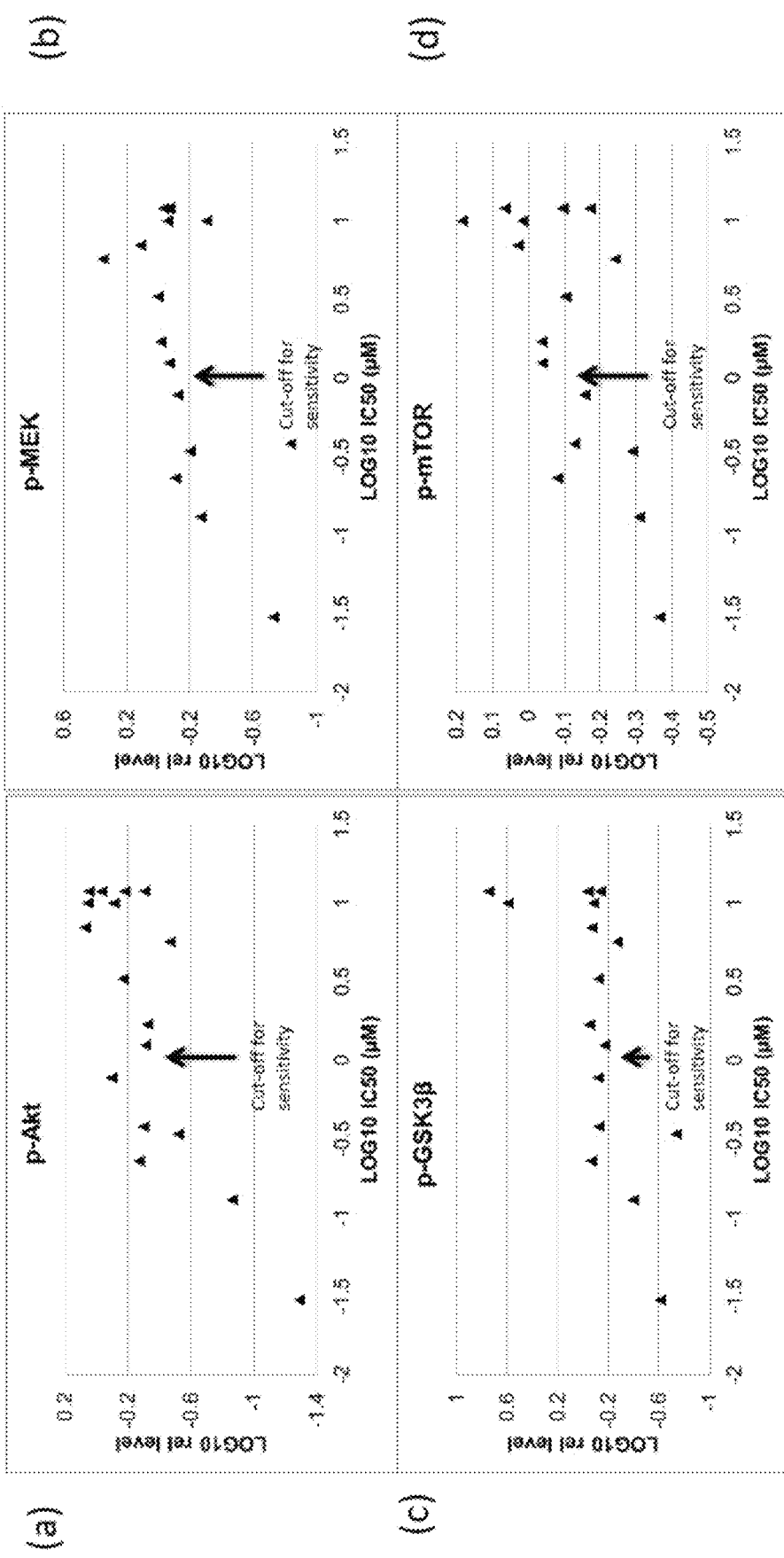
FIGS. 2(a)-(d) show the relative levels of optimal biomarkers as a function of IC50 values for the 1 hour time point (cut off for sensitivity is 1 uM). Each point on the graphs represents a cell line.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine.

A "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes and/or to predict responsiveness or non-responsiveness to a particular therapeutic regimen). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit. A sample that is assayed in the diagnostic methods of the present invention may be obtained from any suitable patient, including but not limited to a patient suspected of having breast cancer or a patient having a predisposition to breast cancer. The patient may or may not exhibit symptoms associated with one or more of these conditions.

"Level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker.

As used herein, the term "cancer" is intended to mean a class of diseases characterized by the uncontrolled growth of aberrant cells, including all known cancers, and neoplastic conditions, whether characterized as malignant, benign, soft tissue or solid tumor. Aside from non-melanoma skin cancer, breast cancer is the most common cancer among women in the United States. It is also one of the leading causes of cancer death among women of all races and Hispanic origin populations. About 1 in 8 (12%) women in the US will develop invasive breast cancer during their lifetime. The American Cancer Society estimates that in 2013 about 232,340 new cases of invasive breast cancer will be diagnosed in women, about 64,640 new cases of carcinoma in situ (CIS) will be diagnosed (CIS is non-invasive and is the earliest form of breast cancer), and about 39,620 women will die from breast cancer. Breast cancer is the second leading cause of cancer death in women, second only to lung cancer. The chance that breast cancer will be responsible for a woman's death is about 1 in 36 (about 3%). Death rates from breast cancer have been declining since about 1989, with larger decreases in women younger than 50. These decreases are believed to be the result of earlier detection through screening and increased awareness, as well as improved treatment.

The levels of pharmacodynamic markers can be assessed to determine the effects of investigational agents, assaying tumors directly or surrogate tissues such as plasma. The ultimate goal is to incorporate predictive pharmacodynamic markers in early clinical studies of new oncology drugs. This would allow early evaluation of investigational agents based on human pharmacology data in a 'real time' setting. The biomarkers identified herein can be used for cancer diagnostics, e.g., to predict (prior to treatment) and/or determine (after commencement of treatment) whether a cancer is resistant to a specific course of treatment. The following biomarkers were identified as valuable in the diagnosis and prediction of responsiveness to treatment for breast cancer (i) total and phosphorylated forms of Akt, MEK, mTOR, GSK3beta, and combinations thereof, (ii) p70S6K, eIF4EBP1, PTEN, and (iii) combinations thereof. The invention includes the use of these biomarkers to indicate if treatment with a therapeutic regimen targeting EGFR tyrosine kinase activity results in responsive or non-responsive outcomes.

Accordingly, the present invention includes a method and kit configured to measure the levels of one or more of (i) total and phosphorylated isoforms of Akt, MEK, mTOR, GSK3beta, and combinations thereof, (ii) p70S6K, eIF4EBP1, PTEN, and (iii) combinations thereof to determine if a tumor is responsive and/or non-responsive to treatment with drugs targeting EGFR tyrosine kinase activity (e.g., gefitinib). In addition, the invention also relates to methods and kits to detect abnormal EGFR tyrosine kinase activity in a patient and/or to detect an alteration in EGFR tyrosine kinase activity by measuring one or more of the biomarkers identified above and comparing those levels to a normal control and/or a baseline level to determine if an abnormality or alteration is present in a patient sample.

Therefore, the invention provides a method for evaluating the efficacy of a treatment regimen in a patient diagnosed with breast cancer, said method comprising (a) measuring a level of a biomarker in a test sample obtained from a patient undergoing said treatment regimen for breast cancer, wherein said biomarker is selected from the group consisting of (i) total and phosphorylated isoforms of Akt, MEK, mTOR, GSK3beta, and combinations thereof, (ii) p70S6K, eIF4EBP1, PTEN, and (iii) combinations thereof; and (b) evaluating from said level whether said patient is responsive to said treatment regimen.

The methods may include measuring a level of two or more biomarkers, or a panel of three or more such biomarkers. The panel may further comprise one or more additional biomarkers selected from HER2/neu, ER, PR, Ki67, and combinations thereof. Additional diagnostic methods can be used in combination with the panels described herein, as referenced in Misek et al, Int J. Proteomics, Vol. 2011, Article ID 343582, pages 1-9, the disclosure of which is incorporated herein by reference in its entirety.

In one embodiment, the method includes measuring a level of a first biomarker and an additional biomarker, wherein the first biomarker is a total form of a biomarker and the additional biomarker is a phosphorylated form of that biomarker. Diagnosis of the presence or state of a cancer could be based on the absolute levels of one or both of these forms. Alternatively, the diagnosis could be based on the ratio of phosphorylated to total forms (i.e., based on the fraction of a specific biomarker that is present in a phosphorylated form). In one example, the method may include measuring a level of total Akt as the first biomarker and measuring a level of phosphorylated Akt as the additional biomarker. Similarly, the method may comprise measuring one or more of the following pairs of first and additional biomarkers, i.e., total and phosphorylated biomarkers: total MEK and phosphorylated MEK; total GSK3β and phosphorylated GSK3β; and total mTOR and phosphorylated mTOR.

The level(s) of the various biomarkers identified herein may reflect the responsiveness or non-responsiveness of breast cancer to a given treatment regimen. A response to a therapeutic regimen includes a detectable reduction to some extent of one or more of the symptoms of breast cancer, including, but not limited to: (1) reduction in the number of cancer cells; (2) reduction in tumor size; (3) inhibition (i.e., slowing to some extent, preferably stopping) of cancer cell infiltration into peripheral organs; (4) inhibition (i.e., slowing to some extent, preferably stopping) of tumor metastasis; (5) inhibition, to some extent, of tumor growth; (6) relieving or reducing to some extent one or more of the symptoms associated with the disorder; and/or (7) increasing, to some extent, the overall survival of a patient relative to that observed for the standard of care for Breast cancer. A response to a therapeutic regimen may also comprise maintenance of a therapeutic benefit, including, but not limited to (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder and/or (6) inhibiting a recurrence or onset of one or more of the symptoms associated with the disorder.

The therapeutic regimen used in the method of the present invention may include radiation treatment, chemotherapy, treatment with therapeutic drugs, immune system modulation or other therapeutic regimens used in cancer treatment. In one embodiment, the therapeutic regimen comprises administration of a therapeutic agent that modulates one or more biological activities and the level(s) of said one or more biomarkers indicate modulation of said biological activities by said therapeutic agent. In particular, the biological activity includes EGFR tyrosine kinase activity and the therapeutic agent may be an agonist or an antagonist of such signaling pathway(s). In a preferred embodiment, the therapeutic agent is gefitinib (Iressa), and it can be administered alone or in combination with one or more additional therapeutic agents, e.g., trastuzumab, aromasin, anastrazole, taxotere (or another taxane), doxorubicin, adriamycin, cytoxan, methotrexate, fluorouracil, and combinations thereof.

The therapeutic regimen may include administration of a therapeutic agent or a combination of therapeutic agents to a patient one or more times over a given time period. For example, if the therapeutic agent is gefitinib, one suitable therapeutic regimen comprises administering the drug once daily until the patient is no longer clinically benefiting from treatment or until unacceptable toxicity occurs. This treatment regimen may be accompanied by the administration of one or more additional chemotherapeutic agents or palliative agents. The level(s) of biomarkers may be measured before treatment, one or more times during the administration period, and/or after treatment is suspended. The level(s) of biomarkers may be measured at one or more time points in the treatment regimen, e.g., before treatment, one or more times during the four week administration period, and/or after the four week administration period. Therefore, the method may include measuring an interim level of a biomarker during the therapeutic regimen and the evaluating step further comprises comparing that level, the interim level and the baseline level.

In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the evaluating step further comprises comparing the level and the baseline level. Moreover, the method may further comprise measuring an interim level of the biomarker during the therapeutic regimen and the evaluating step further comprises comparing the level, the interim level and the baseline level.

Alternatively, the measuring step may comprise measuring a level(s) of a biomarker before a therapeutic regimen is initiated to predict whether breast cancer will be responsive or non-responsive to a given therapeutic regimen. The method may further comprise modifying the therapeutic regimen based on the level(s) of a biomarker observed during the measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

Still further, the evaluating step may include comparing the level of a biomarker to a detection cut-off level, wherein a level above the detection cut-off level is indicative of breast cancer. Alternatively, the evaluating step comprises comparing a level of a biomarker to a detection cut-off level, wherein a level below the detection cut-off level is indicative of breast cancer.

In one embodiment of the present invention, the level of a biomarker is compared to a detection cut-off level or range, wherein the biomarker level above or below the detection cut-off level (or within the detection cut-off range) is indicative of breast cancer. Furthermore, the levels of two or more biomarkers may both be used to make a determination. For example, i) having a level of at least one of the markers above or below a detection cut-off level (or within a detection cut-off range) for that marker is indicative of breast cancer; ii) having the level of two or more (or all) of the markers above or below a detection cut-off level (or within a detection cut-off range) for each of the markers is indicative of breast cancer; or iii) an algorithm based on the levels of the multiple markers is used to determine if breast cancer is present.

As described herein, the measured levels of one or more biomarkers may be used to detect or monitor cancer (e.g., breast cancer) and/or to determine the responsiveness of a cancer to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a cancer and which reports such determination(s) back to the user.

In addition, the methods of the present invention may be used in combination with other methods of diagnosing breast cancer in a patient. In one embodiment, the patient may also be subjected to one or more diagnostic tools designed to detect breast cancer. For example, imaging methods may be used to provide images of the breast to look for tumors. In addition, a biopsy may be performed. Imaging methods that may be performed include ultrasound, computed tomography (CT) scan and magnetic resonance imaging (MRI).

The assays of the present invention may be conducted by any suitable method. In one embodiment, the measuring step is conducted on a single sample, and it may be conducted in a single assay chamber or assay device, including but not limited to a single well of an assay plate, a single assay cartridge, a single lateral flow device, a single assay tube, etc.

According to one aspect of the invention, the level(s) of biomarker(s) are measured in samples collected from individuals clinically diagnosed with, suspected of having or at risk of developing breast cancer. Initial diagnosis may have been carried out using conventional methods, e.g., biopsy or other conventional diagnostic methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, kidney cancer, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥0.8. In another embodiment, a biomarker provides an AUC≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric inter-quartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, Meso Scale Discovery, a division of Meso Scale Diagnostics, LLC, Rockville, Md.).

The present invention relates to a kit for the analysis of a panel of target analytes. The kit is preferably configured to conduct a multiplexed assay of two or more of the following analytes: (i) total and phosphorylated isoforms of Akt, MEK, mTOR, GSK3beta, and combinations thereof, (ii) p70S6K, eIF4EBP1, PTEN, and (iii) combinations thereof. The kit can include (a) a single panel arrayed on a multi-well plate which is configured to be used in an electrochemiluminescence assay, as well as (b) associated consumables, e.g., detection antibodies, calibrators, and optional diluents and/or buffers. Alternatively, the multi-well plates and associated consumables can be provided separately.

The panel is preferably configured in a multi-well assay plate including a plurality of wells, each well having an array with "spots" or discrete binding domains. Preferably, the array includes one, four, seven, ten, sixteen, or twenty-five binding domains, and most preferably, the array includes one, four, seven, or ten binding domains. A capture antibody to each analyte is immobilized on a binding domain in the well and that capture antibody is used to detect the presence of the target analyte in an immunoassay. Briefly, a sample suspected of containing that analyte is added to the well and if present, the analyte binds to the capture antibody at the designated binding domain. The presence of bound analyte on the binding domain is detected by adding labeled detection antibody. The detection antibody also binds to the analyte forming a "sandwich" complex (capture antibody-analyte-detection antibody) on the binding domain.

The multiplexed immunoassay kits described herein allow a user to simultaneously quantify multiple biomarkers. The panels are selected and optimized such that the individual assays function well together. The sample may require dilution prior to being assayed. Sample dilutions for specific sample matrices of interest are optimized for a given panel to minimize sample matrix effects and to maximize the likelihood that all the analytes in the panel will be within the dynamic range of the assay. In a preferred embodiment, all of the analytes in the panel are analyzed with the same sample dilution in at least one sample type. In another preferred embodiment, all of the analytes in a panel are measured using the same dilution for most sample types.

For a given panel, the detection antibody concentration and the number of labels per protein (L/P ratio) for the detection antibody are adjusted to bring the expected levels of all analytes into a quantifiable range at the same sample dilution. If one wants to increase the high end of the quantifiable range for a given analyte, then the L/P can be decreased and/or the detection antibody concentration is decreased. On the other hand, if one wants to increase the lower end of the quantifiable range, the UP can be increased, the detection antibody concentration can be increased if it is not at the saturation level, and/or the background signal can be lowered.

Calibration standards for use with the assay panels are selected to provide the appropriate quantifiable range with the recommended sample dilution for the panel. The calibration standards have known concentrations of one of more of the analytes in the panel. Concentrations of the analytes in unknown samples are determined by comparison to these standards. In one embodiment, calibration standards comprise mixtures of the different analytes measured by an assay panel. Preferably, the analyte levels in a combined calibrator are selected such that the assay signals for each analyte are comparable, e.g., within a factor of two, a factor of five or a factor of 10. In another embodiment, calibration standards include mixtures of analytes from multiple different assay panels.

A calibration curve may be fit to the assay signals measured with calibration standards using, e.g., curve fits known in the art such as linear fits, 4-parameter logistic (4-PL) and 5-parameter (5-PL) fits. Using such fits, the concentration of analytes in an unknown sample may be determined by backfitting the measured assay signals to the calculated fits. Measurements with calibration standards may also be used to determine assay characteristics such as the limit of detection (LOD), limit of quantification (LOQ), dynamic range, and limit of linearity (LOL).

A kit can include the following assay components: a multi-well assay plate configured to conduct an immunoassay for one of the panels described herein, a set of detection antibodies for the analytes in the panel (wherein the set comprises individual detection antibodies and/or a composition comprising a blend of one or more individual detection antibodies), and a set of calibrators for the analytes in the panel (wherein the set comprises individual calibrator protein compositions and/or a composition comprising a blend of one or more individual calibrator proteins). The kit can also include one of more of the following additional components: a blocking buffer (used to block assay plates prior to addition of sample), an antibody diluent (used to dilute stock detection antibody concentrations to the working concentration), an assay diluent (used to dilute samples), a calibrator diluent (used to dilute or reconstitute calibration standards) and a read buffer (used to provide the appropriate environment for detection of assay labels, e.g., by an ECL measurement). The antibody and assay diluents are selected to reduce background, optimize specific signal, and reduce assay interference and matrix effect. The calibrator diluent is optimized to yield the longest shelf life and retention of calibrator activity. The blocking buffer should be optimized to reduce background. The read buffer is selected to yield the appropriate sensitivity, quantifiable range, and slowest off-rate.

The reagent components of the kit can be provided as liquid reagents, lyophilized, or combinations thereof, diluted or undiluted, and the kit includes instructions for appropriate preparation of reagents prior to use. In a preferred embodiment, a set of detection antibodies are included in the kit comprising a plurality of individual detection antibody compositions in liquid form. Moreover, the set of calibrators provided in the kit preferably comprise a lyophilized blend of calibrator proteins. Still further, the kit includes a multi-well assay plate that has been pre-coated with capture antibodies and exposed to a stabilizing treatment to ensure the integrity and stability of the immobilized antibodies.

As part of a multiplexed panel development, assays are optimized to reduce calibrator and detection antibody non-specific binding. In sandwich immunoassays, specificity mainly comes from capture antibody binding. Some considerations for evaluating multiplexed panels include: (a) detection antibody non-specific binding to capture antibodies is reduced to lower background of assays in the panel, and this can be achieved by adjusting the concentrations and L/P of the detection antibodies; (b) non-specific binding of detection antibodies to other calibrators in the panel is also undesirable and should be minimized; (c) non-specific binding of other calibrators in the panel and other related analytes should be minimized; if there is calibrator non-specific binding, it can reduce the overall specificity of the assays in the panel and it can also yield unreliable results as there will be calibrator competition to bind the capture antibody.

Different assays in the panel may require different incubation times and sample handling requirements for optimal performance. Therefore, the goal is to select a protocol that's optimized for most assays in the panel. Optimization of the assay protocol includes, but is not limited to, adjusting one or more of the following protocol parameters: timing (incubation time of each step), preparation procedure (calibrators, samples, controls, etc.), and number of wash steps.

The reagents used in the kits, e.g., the detection and capture antibodies and calibrator proteins, are preferably subjected to analytical testing and meet or exceed the specifications for those tests. The analytical tests that can be used to characterize kit materials include but are not limited to, CIEF, DLS, reducing and/or non-reducing EXPERION, denaturing SDS-PAGE, non-denaturing SDS-PAGE, SEC-MALS, and combinations thereof. In a preferred embodiment, the materials are characterized by CIEF, DLS, and reducing and non-reducing EXPERION. One or more additional tests, including but not limited to denaturing SDS-PAGE, non-denaturing SDS-PAGE, SEC-MALS, and combinations thereof, can also be used to characterize the materials. In a preferred embodiment, the materials are also subjected to functional testing, i.e., a binding assay for the target analyte, as well as one or more characterization tests, such as those listed above. If the materials do not meet or exceed the specifications for the functional and/or characterization tests, they can be subjected to additional purification steps and re-tested. Each of these tests and the metrics applied to the analysis of raw materials subjected to these tests are described below:

Capillary Isoelectric Focusing (CIEF) is a technique commonly used to separate peptides and proteins, and it is useful in the detection of aggregates. During a CIEF separation, a capillary is filled with the sample in solution and when voltage is applied, the ions migrate to a region where they become neutral (pH=pI). The anodic end of the capillary sits in acidic solution (low pH), while the cathodic end sits in basic solution (high pH). Compounds of equal isoelectric points (pI) are "focused" into sharp segments and remain in their specific zone, which allows for their distinct detection based on molecular charge and isoelectric point. Each specific antibody solution will have a fingerprint CIEF that can change over time. When a protein solution deteriorates, the nature of the protein and the charge distribution can change. Therefore, CIEF is a particularly useful tool to assess the relative purity of a protein solution and it is a preferred method of characterizing the antibodies and calibrators in the plates and kits described herein. The metrics used in CIEF include pI of the main peak, the pI range of the solution, and the profile shape, and each of these measurements are compared to that of a reference standard.

Dynamic Light Scattering (DLS) is used to probe the diffusion of particulate materials either in solution or in suspension. By determining the rate of diffusion (the diffusion coefficient), information regarding the size of particles, the conformation of macromolecular chains, various interactions among the constituents in the solution or suspension, and even the kinetics of the scatterers can be obtained without the need for calibration. In a DLS experiment, the fluctuations (temporal variation, typically in a µs to ms time scale) of the scattered light from scatterers in a medium are recorded and analyzed in correlation delay time domain. Like CIEF, each protein solution will generate a fingerprint DLS for the particle size and it's ideally suited to detect aggregation. All IgGs, regardless of binding specificity, will exhibit the same DLS particle size. The metrics used to analyze a protein solution using DLS include percentage polydispersity, percentage intensity, percentage mass, and the radius of the protein peak. In a preferred embodiment, an antibody solution meets or exceeds one or more of the following DLS specifications: (a) radius of the antibody peak: 4-8 nm (antibody molecule size); (b) polydispersity of the antibody peak: <40% (measure of size heterogeneity of antibody molecules); (c) intensity of the antibody peak: >50% (if other peaks are present, then the antibody peak is the predominant peak); and (d) mass in the antibody peak: >50%.

Reducing and non-reducing gel electrophoresis are techniques well known in the art. The EXPERION™ (Bio-Rad Laboratories, Inc., www.bio-rad.com) automated electrophoresis station performs all of the steps of gel-based electrophoresis in one unit by automating and combining electrophoresis, staining, destaining, band detection, and imaging into a single step. It can be used to measure purity. Preferably, an antibody preparation is greater 50% pure by Experion, more preferably, greater than 75% pure, and most preferably greater than 80% pure. Metrics that are applied to protein analysis using non-reducing Experion include percentage total mass of protein, and for reducing Experion they include percentage total mass of the heavy and light chains in an antibody solution, and the heavy to light chain ratio.

Multi-Angle Light Scattering (MALS) detection can be used in the stand-alone (batch) mode to measure specific or non-specific protein interactions, as well as in conjunction with a separation system such as flow field flow fractionation (FFF) or size exclusion chromatography (SEC). The combined SEC-MALS method has many applications, such as the confirmation of the oligomeric state of a protein, quantification of protein aggregation, and determination of protein conjugate stoichiometry. Preferably, this method is used to detect molecular weight of the components of a sample.

As used herein, a lot of kits comprise a group of kits comprising kit components that meet a set of kit release specifications. A lot can include at least 10, at least 100, at least 500, at least 1,000, at least 5,000, or at least 10,000 kits and a subset of kits from that lot are subjected to analytical testing to ensure that the lot meets or exceeds the release specifications. In one embodiment, the release specifications include but are not limited to kit processing, reagent stability, and kit component storage condition specifications. Kit processing specifications include the maximum total sample incubation time and the maximum total time to complete an assay using the kit. Reagent stability specifications include the minimum stability of each reagent component of the kit at a specified storage temperature. Kit storage condition specifications include the range of storage temperatures for all components of the kit, the maximum storage temperature for frozen components of the kit, and the maximum storage temperature for non-frozen components of the kit. A subset of kits in a lot is reviewed in relation to these specifications and the size of the subset depends on the lot size. In a preferred embodiment, for a lot of up to 300 kits, a sampling of 4-7 kits are tested; for a lot of 300-950 kits, a sampling of 8-10 kits are tested; and for a lot of greater than 950 kits, a sampling of 10-12 kits are tested. Alternatively or additionally, a sampling of up to 1-5% preferably up to 1-3%, and most preferably up to 2% is tested.

In addition, each lot of multi-well assay plates is preferably subjected to uniformity and functional testing. A subset of plates in a lot is subjected to these testing methods and the size of the subset depends on the lot size. In a preferred embodiment, for a lot of up to 300 plates, a sampling of 4-7 plates are tested; for a lot of 300-950 plates, a sampling of 8-10 plates are tested; and for a lot of greater than 950 plates, a sampling of 10-12 plates are tested. Alternatively or additionally, a sampling of up to 1-5% preferably up to 1-3%, and most preferably up to 2% is tested. The uniformity and functional testing specifications are expressed in terms of % CV. Coefficient of Variability, which is a dimensionless number defined as the standard deviation of a set of measurements, in this case, the relative signal detected from binding domains across a plate, divided by the mean of the set.

One type of uniformity testing is protein A/G testing. Protein A/G binding is used to confirm that all binding domains within a plate are coupled to capture antibody. Protein A/G is a recombinant fusion protein that combines IgG binding domains of Protein A and protein G and it binds to all subclasses of human IgG, as well as IgA, IgE, IgM and, to a lesser extent, IgD. Protein A/G also binds to all subclasses of mouse IgG but not mouse IgA, IgM, or serum albumin, making it particularly well suited to detect mouse monoclonal IgG antibodies without interference from IgA, IgM, and serum albumin that might be present in the sample matrix. Protein A/G can be labeled with a detectable moiety, e.g., a fluorescent, chemiluminescent, or electrochemiluminescent label, preferably an ECL label, to facilitate detection. Therefore, if capture antibody is adhered to a binding domain of a well, it will bind to labeled protein A/G, and the relative amount of capture antibody bound to the surface across a plate can be measured.

In addition to the uniformity testing described above, a uniformity metric for a subset of plates within a lot can be calculated to assess within-plate trending. A uniformity metric is calculated using a matrix of normalized signals from protein A/G and/or other uniformity or functional tests. The raw signal data is smoothed by techniques known in the art, thereby subtracting noise from the raw data, and the uniformity metric is calculated by subtracting the minimum signal in the adjusted data set from the maximum signal.

In a preferred embodiment, a subset of plates in a lot is subjected to protein A/G and functional testing and that subset meet or exceed the following specifications:

TABLE 3(a)

Plate Metrics

| Metric | Preferred Specification for a subset of 96 well multi-well plates |
| --- | --- |
| Average intraplate CV | ≤10% |
| Maximum intraplate CV | ≤13% |
| Average Uniformity | ≤25% |
| Maximum Uniformity | ≤37% |
| CV of intraplate averages | ≤18% |
| Signal, lower boundary | >1500 |
| Signal, upper boundary | <10$^{(6)}$ |

As disclosed in U.S. Pat. No. 7,842,246 to Wohlstadter et al., the disclosure of which is incorporated herein by reference in its entirety, each plate consists of several elements, e.g., a plate top, a plate bottom, wells, working electrodes, counter electrodes, reference electrodes, dielectric materials, electrical connects, and assay reagents. The wells of the plate are defined by holes/openings in the plate top. The plate bottom can be affixed, manually or by automated means, to the plate top, and the plate bottom can serve as the bottom of the well. Plates may have any number of wells of any size or shape, arranged in any patter or configuration, and they can be composed of a variety of different materials. Preferred embodiments of the invention use industry standard formats for the number, size, shape, and configuration of the plate and wells. Examples of standard formats include 96, 384, 1536, and 9600 well plates, with the wells configured in two-dimensional arrays. Other formats may include single well plates (preferably having a plurality of assay domains that form spot patterns within each well), 2 well plates, 6 well plates, 24 well plates, and 6144 well plates. Each well of the plate includes a spot pattern of varying density, ranging from one spot within a well to 2, 4, 7, 9, 10, 16, 25, etc., as described hereinabove.

Each plate is assembled according to a set of preferred specifications. In a preferred embodiment, a plate bottom meets or exceeds the following specifications:

TABLE 3(b)

Plate bottom specifications

| Parameter | 96-well (round well) specifications in inches |
| --- | --- |
| Length range (C to C)* | 3.8904-3.9004 (A1-A12 and H1-H12)** |
| Width range (C to C) | 2.4736-2.4836 (A1-A12 and H1-H12) |
| Well to well spacing | 0.3513-0.3573 |

*C to C well distance is the center of spot to center of spot distance between the outermost wells of a plate.

In a further preferred embodiment, the plate also meets or exceeds defined specifications for alignment of a spot patter within a well of the plate. These specifications include three parameters: (a) $\Delta x$, the difference between the center of the spot pattern and the center of the well along the x axis of the plate (column-wise, long axis); (b) $\Delta y$, the difference between the center of the spot pattern and the center of the well along the y axis of the plate (row-wise, short axis); and (c) $\alpha$, the counter-clockwise angle between the long axis of the plate bottom and the long axis of the plate top of a 96-well plate. In a preferred embodiment, the plate meets or exceeds the following specifications: $\Delta x \leq 0.2$ mm, $\Delta y \leq 0.2$ mm, and $\alpha \leq 0.1°$.

The following non-limiting examples serve to illustrate rather than limit the present invention.

EXAMPLES

Measurement of Biomarkers Indicative of Gefitinib Sensitivity in the Treatment of Breast Cancer Multiplex immunoassay kits were used for detection of total and/or phosphorylated biomarkers (supplied by Meso Scale Diagnostics, LLC., Rockville, Md.). Levels of each biomarker were determined by calibration of the assays with were either purified calibrator proteins or using control cell lysates from appropriately treated cultured cell lines (e.g., cells subjected to conditions known to induce or reduce levels of a specific biomarker). Calibration curves were derived by testing serial dilutions of the calibrator lysates or purified proteins. Levels of biomarkers in test samples were back-calculated from the calibration curves and were expressed in terms of wt. (or arbitrary units) of protein per weight of tissue extract (for purified calibrators) or in terms of weight of crude control lysate protein per well (for lysate calibrators). Titrations of tumor extracts were carried out to determine the linearity of the assay response to sample dilution and to select the sample dilution that would be appropriate to use for each assay panel.

The following cell lines were used, representing different breast cancer subtypes and having known differences in sensitivity to gefitinib as indicated by their IC50 values. Cells were treated with 1 uM gefitinib.

TABLE 4

| Cell Line | Sub-type | IC50 (μM) | HER2 | ER |
|---|---|---|---|---|
| MDA-MB-175 | Luminal | 0.03 | − | + |
| BT-474 | HER2 amplified | 0.13 | + | − |
| HCC1954 | HER2 amplified | 0.23 | + | − |
| SKBR3 | HER2 amplified | 0.34 | + | − |
| SUM190 | HER2 amplified | 0.38 | + | − |
| MDA-MB-468 | Basal/EGFR amplified | 0.78 | − | − |
| UACC812 | HER2 amplified | 1.25 | + | − |

TABLE 5

Correlation coefficients for changes in levels of each marker versus IC50 values for the 17 breast cancer cell lines evaluated at individual time points. The sums of the correlation coefficients for each marker are shown.

| | p-Akt | p-MEK | p-GSK3? | p-mTOR | mTOR | p-p70S6K | MEK | p-4EBP1 | Akt | p-EGFR | IGF1R | p70S6K | VEGF |
|---|---|---|---|---|---|---|---|---|---|---|---|---|---|
| 10 min | 0.70 | 0.59 | 0.49 | 0.24 | −0.16 | 0.36 | −0.14 | 0.31 | −0.05 | −0.18 | 0.01 | −0.10 | 0.19 |
| 0.5 h | 0.75 | 0.71 | 0.54 | 0.48 | 0.35 | 0.50 | 0.31 | 0.29 | 0.43 | 0.41 | 0.20 | 0.18 | 0.60 |
| 1 h | 0.79 | 0.62 | 0.63 | 0.66 | 0.59 | 0.56 | 0.47 | 0.58 | 0.17 | 0.63 | 0.50 | 0.20 | 0.37 |
| 8 h | 0.79 | 0.57 | 0.69 | 0.65 | 0.44 | 0.55 | 0.55 | 0.34 | 0.32 | 0.50 | 0.25 | 0.14 | 0.24 |
| 24 h | 0.71 | 0.56 | 0.56 | 0.51 | 0.42 | 0.21 | 0.41 | 0.04 | 0.47 | −0.19 | 0.24 | 0.38 | 0.17 |
| 48 h | 0.64 | 0.62 | 0.58 | 0.61 | 0.78 | 0.16 | 0.57 | 0.51 | 0.69 | 0.57 | 0.47 | 0.75 | −0.01 |
| SUM | 4.38 | 3.68 | 3.49 | 3.16 | 2.43 | 2.35 | 2.17 | 2.07 | 2.04 | 1.73 | 1.67 | 1.55 | 1.55 |

| | VEGFR2 | p-PTEN | Raptor | GSK3? | Rictor | PTEN | EGFR | ERK | PI3K | p-IGF1R | 4EBP1 | cMet |
|---|---|---|---|---|---|---|---|---|---|---|---|---|
| 10 min | 0.23 | 0.02 | 0.06 | −0.41 | −0.19 | −0.20 | −0.23 | 0.16 | −0.37 | 0.07 | −0.13 | −0.30 |
| 0.5 h | 0.48 | 0.17 | −0.01 | −0.37 | 0.18 | −0.02 | −0.01 | 0.03 | −0.45 | 0.13 | −0.02 | 0.07 |
| 1 h | 0.04 | 0.41 | −0.05 | 0.29 | 0.10 | 0.38 | 0.24 | 0.13 | 0.06 | | 0.07 | 0.04 |
| 8 h | 0.22 | 0.25 | 0.07 | 0.15 | −0.12 | 0.04 | −0.06 | −0.26 | 0.25 | −0.20 | −0.36 | 0.07 |
| 24 h | 0.21 | 0.23 | 0.00 | 0.27 | 0.01 | 0.00 | −0.18 | −0.05 | | −0.20 | −0.09 | −0.41 |
| 48 h | 0.12 | 0.17 | 0.62 | 0.52 | 0.31 | 0.00 | 0.21 | −0.17 | 0.25 | −0.09 | 0.25 | 0.15 |
| SUM | 1.30 | 1.24 | 0.69 | 0.47 | 0.30 | 0.21 | −0.02 | −0.16 | −0.26 | −0.29 | −0.29 | −0.38 |

TABLE 4-continued

| Cell Line | Sub-type | IC50 (μM) | HER2 | ER |
|---|---|---|---|---|
| T47D | Luminal | 1.7 | − | + |
| CAL 51 | Basal/vimentin+ | 3.3 | − | − |
| MDA-MB-453 | HER2 amplified | 5.7 | + | − |
| ZR75-1 | Luminal | 7 | − | + |
| HCC1937 | Basal | 10 | − | − |
| EFM19 | Luminal | 10 | − | + |
| BT20 | Basal | >10 | − | − |
| MCF7 | Luminal | >10 | − | + |
| MDA-MB-231 | Basal/vimentin+ | >10 | − | − |
| CAMA1 | Luminal | >10 | − | + |

In general, the assay format was as follows, with minor alterations for specific assay panels as indicated in the assay protocols provided with each assay kit (supplied by Meso Scale Diagnostics, LLC): (1) block MSD MULTI-SPOT® plate for 1 hour with appropriate MSD® blocking solution and wash; (2) add 25 μl assay diluent to each well, if specified; (3) add 25 μl calibrator, or sample (diluted as appropriate) to each well; (4) incubate with shaking for 1-3 hours (time as specified) and wash the well; (5) add 25 μl labeled detection antibody solution to each well; (6) incubate with shaking for 1-2 hours (time as specified) and wash the well; (7) add 150 μl MSD read buffer to each well; (8) read plate immediately on MSD S16000 Reader (supplied by Meso Scale Diagnostics, LLC).

Fractional marker levels (to 0 h time point) for a representative set of biomarkers is shown in FIG. 1. The levels of several markers (e.g., phospho-Akt, phospho-GSK3beta, phospho-MEK, and phospho-mTOR, were decreased correlating with IC50 values.

The fractional levels of each biomarker (relative to the t=0 h values) in each cell line were correlated to the known gefitinib IC50 values for the cells lines. Table 5 summarizes the correlation coefficients for each of the markers at each of the time points analyzed across all of the cell lines' IC50 values. The sums of the correlation coefficients for each marker suggest which markers change in levels over multiple time points indicating a persistent response to drug. The top four markers were found to be phospho-Akt, phospho-GSK3beta, phospho-MEK, and phospho-mTOR.

Figure 3:
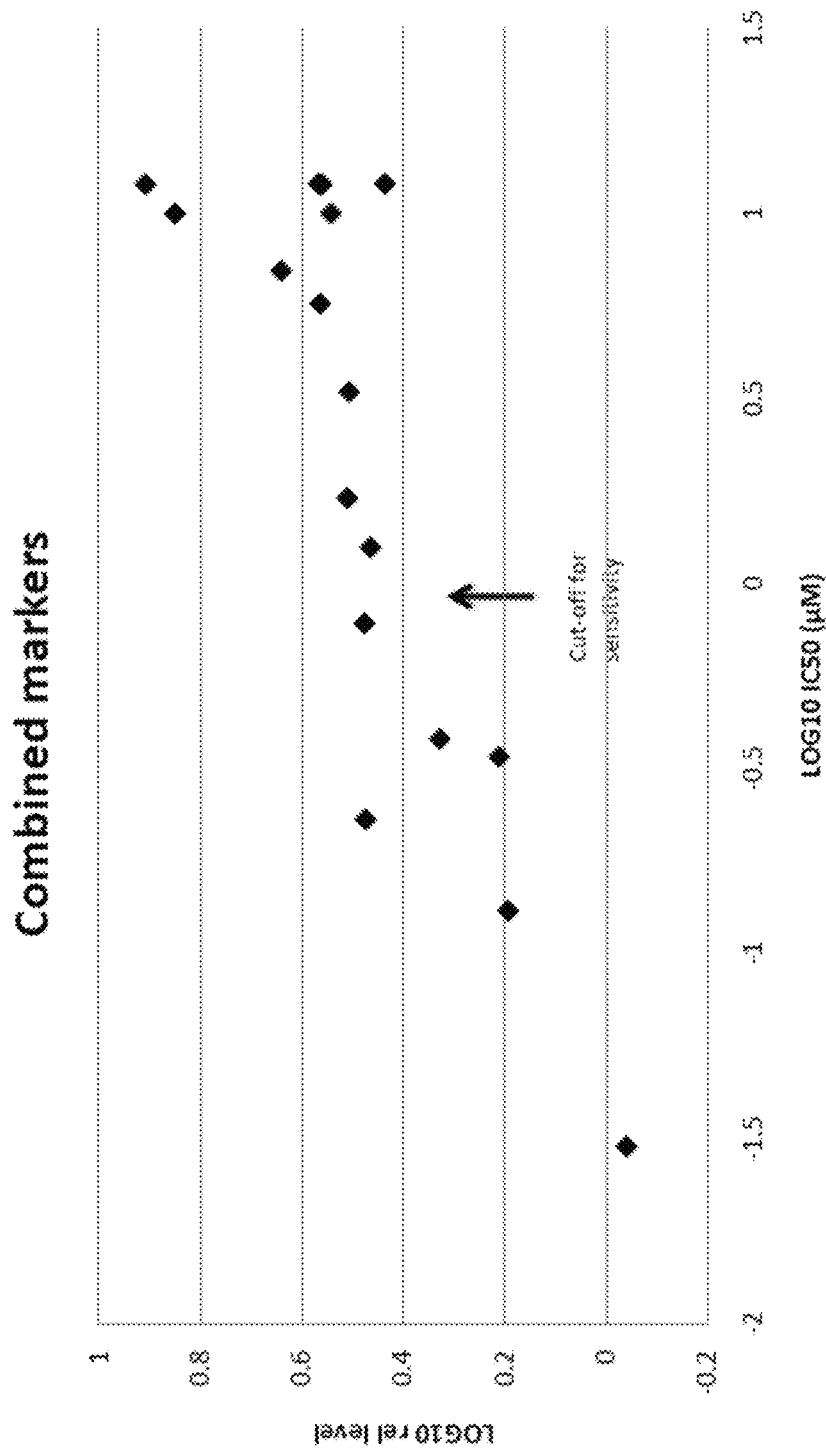
FIG. 3 shows the relative levels of the combined markers phospho-Akt, phospho-GSK3beta, phospho-MEK, and phospho-mTOR as a function of IC50 values for the 1 hour time point. Each point on the graph represents the sum of the relative levels of each marker shown in FIG. 2(a)-(d) for one cell line as a function of its IC50 value for gefitinib.

The relative levels of optimal biomarkers as a function of IC50 values for the 1 hour time point are illustrated in FIGS. 2(a)-(d) (cut off for sensitivity is 1 uM). Each point on the graphs represents a cell line. The relative levels of the combined markers phospho-Akt, phospho-GSK3beta, phospho-MEK, and phospho-mTOR as a function of IC50 values for the 1 hour time point is illustrated in FIG. 3. Each point on the graph represents the sum of the relative levels of each marker shown in FIG. 2(a)-(d) for one cell line as a function of its IC50 value for gefitinib.

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

The invention claimed is:

1. A method of administering a treatment regimen to a patient in need thereof for treating breast cancer, comprising:
    (a) obtaining a first test sample from said patient before said treatment regimen is initiated, wherein said treatment regimen comprises administration of a therapeutic agent comprising gefitinib;

(b) measuring in said first test sample baseline levels of a plurality of biomarkers comprising phosphorylated isoforms of Akt, MEK, mTOR, and GSK3beta, (c) obtaining an interim test sample from said patient during said treatment regimen for breast cancer, (d) measuring interim levels of said plurality of biomarkers in said interim test sample, (e) comparing said interim levels to said baseline levels of said plurality of biomarkers, (f) evaluating from said comparing step (e) whether said patient is responsive to said treatment regimen, wherein if said interim levels of phosphorylated isoforms of Akt, MEK, mTOR, and GSK3beta are decreased as compared to said baseline levels, then the patient is responsive to said treatment regimen, and wherein if said interim levels of phosphorylated isoforms of Akt, MEK, mTOR, and GSK3beta are unchanged as compared to said baseline levels, then the patient is not responding to said treatment; and performing one of steps (g) or (h)

(g) administering the treatment regimen until the patient is no longer clinically benefitting from treatment or until unacceptable toxicity occurs if the patient is evaluated as being responsive in step (f), or (h) suspending administration of the treatment regimen if the patient is evaluated as being non-responsive in step (f).

2. The method of claim 1, wherein said measuring step comprises conducting a multiplexed assay measurement of a plurality of said biomarkers in said test sample, wherein said multiplexed assay measurement is conducted using one reaction volume comprising said test sample.

3. The method of claim 1, further comprising determining from said interim levels of said plurality of biomarkers the disease progression of breast cancer.

4. The method of claim 1, wherein each measuring step measures said level using a multi-well assay plate.

5. The method of claim 4, wherein each well of said multi-well assay plate comprises a plurality of assay domains, at least two of said assay domains comprising reagents for measuring different biomarkers.

6. The method of claim 5, wherein said assay domains are positioned on an electrode within said well.

7. The method of claim 1, wherein each measuring step comprises performing an immunoassay.

8. The method of claim 1, wherein each measuring step comprises measuring said level using an assay cartridge for conducting a plurality of assays, said cartridge comprising a flow cell having an inlet, an outlet and a detection chamber, said inlet, detection chamber, and outlet defining a flow path through said flow cell, said detection chamber configured to measure said level of biomarkers in said sample.

9. The method of claim 1, wherein each measuring step comprises the use of one or more vials, containers, or compartments, containing labeled detection antibodies specific for said plurality of biomarkers and in one or more vials, containers, or compartments, calibrator proteins.

10. The method of claim 9, wherein said detection antibodies are labeled with an electrochemiluminescent (ECL) label.

11. The method of claim 9, wherein said method further comprises the use of an ECL read buffer.

* * * * *